United States Patent [19]  [11] 4,265,886
Pegel  [45] May 5, 1981

[54] SPIROKETALINS AND THEIR APPLICATIONS

[75] Inventor: Karl H. Pegel, Durban, South Africa

[73] Assignee: Roecar Holdings (Netherlands Antilles (NV), Amsterdam, Netherlands

[21] Appl. No.: 53,736

[22] Filed: Jul. 2, 1979

[30] Foreign Application Priority Data

Jul. 5, 1978 [GB] United Kingdom ............... 28935/78

[51] Int. Cl.$^3$ ..................... A61K 31/705; A61K 31/70
[52] U.S. Cl. ..................................... 424/182; 424/180; 536/5
[58] Field of Search ................ 536/5, 4; 424/180, 182

[56] References Cited

U.S. PATENT DOCUMENTS 2,395,339  2/1946  Marker et al. ........................... 536/5

OTHER PUBLICATIONS

Kintya et al., Chemical Abstracts, vol. 85, 1976 (160461y).
Kintya et al., Chemical Abstracts, vol. 83, 1975 (144506f).
Sofomora et al., Chemical Abstracts, vol. 85, 1976 (78310a).

Primary Examiner—Johnnie R. Brown
Assistant Examiner—Blondel Hazel
Attorney, Agent, or Firm—Cushman, Darby & Cushman

[57] ABSTRACT

The present invention provides a pharmaceutical composition, primarily for the treatment of inflammatory conditions, including benign prostata hypertrophy, the composition containing a spiroketalin such as diosgenyl-β-D-glycoside or hecogenyl-β-D-glycoside. A unit dosage form is provided which contains between 0,3 and 0,75 mgm of the spiroketalin.

11 Claims, No Drawings

SPIROKETALINS AND THEIR APPLICATIONS

FIELD OF THE INVENTION

This invention relates to spiroketalins (3B-hydroxy-5-ene- or 3B-hydroxy -5α-spiroketalsteroid 3-mono- and 3-disaccharides) as well as their monocarboxylic and dicarboxylic acid derived esters as well as their hemiesters, and their application in the treatment of human and animal diseases.

DISCUSSION OF PRIOR ART

Spiroketal steroid glycosides are those 16β,26-dihydroxycholestan-22-one derived steroid saponins which carry a 16,22,26-spiroketal group. They also have a 3β-oxy group involved in the glycoside bond and they carry a double bond or an alpha(α)- or beta(β)-hydrogen in the 5-position. The aglycones of the compounds of this invention have either a 5(6)-double bond or a 5α-hydrogen; typical representatives of the first group are: diosgenin, yamogenin, botogenin and correlogenin, while: tigogenin, neotigogenin, hecogenin and sisalogenin are examples of the second group (1; M. H. Briggs and J. Brotherton in "Steroid Biochemistry and Pharmacology", Academic Press, 1970, pages 288-294. 2; R. Tschesche and G. Wulff in Fortschr. Chem. Org. Naturp., 1973, 30, 461-606).

The naturally occurring saponins of these spiroketalsteroid aglycones are glycosides carrying two or more monosaccharide units in their sugar moiety. This is the reason why these sugar rich saponins usually dissolve readily in water and they frequently give rise to a soap-like froth.

It is known that the intestinal absorption of saponins in general is relatively low and they are not considered toxic on oral comsumption by humans or animals although they may give rise to bloat in animals due to their froth-forming ability. Most saponins are haemolytic when tested in vitro (2). The aglycone diosgenin has been found to be non-toxic in animal experiments with rats, rabbits and chickens, it lowers the serum cholesterol levels in these animals (3; J. L. Diaz-Zagoya et al: Biochem. Pharmacol, 1971, 20, 3473-3480; 4; J. Laguna et al: J. Atheroscl. Res. 1962, 2, 459-470) and its use as a cholesterol lowering agent has been patented (5; DT-OS No. 2348176 and U.S. Pat. No. 3,890,438).

STATEMENT OF THE INVENTION

Therapeutic properties have been described for many members of the saponin family, but never specifically for spiroketalsteroid saponins or spiroketalins. Surprisingly it has now been discovered that certain spiroketalins, that is 3β-mono- or 3β-disaccharide glycosides and their mono- and di- carboxylic acid derived esters, including their hemiesters, of the 5-ene- or 5α-spiroketalsteroid sapogenins with or without an additional keto group at position 12, but without extra free hydroxy groups, show unexpected prophylactic and medicinal properties in the prevention and treatment of various human and animal diseases. Some of these compounds, have as far as the Applicant is aware, never been described in the literature-for example, hecogenin glucoside and the maltosides and lactosides of tigogenin and hecogenin.

The compounds of the invention have the following general formula:

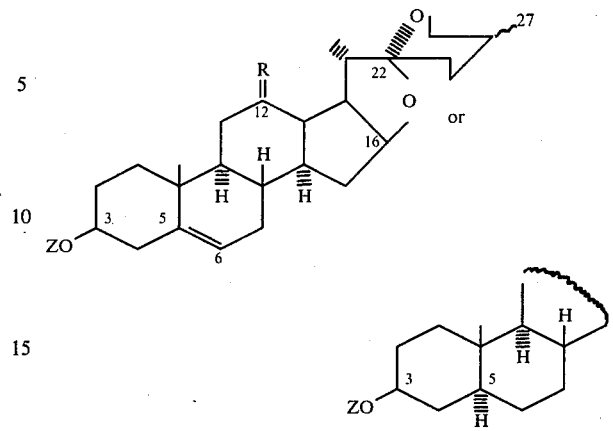

where:
1. either a double bond starts at C-5 or C-5 carriers an alpha hydrogen (5α),
2. Z is the mono- or disaccharide moiety which may be partially or completely esterified with monocarboxylic acids,
3. R represents either two hydrogens or a ketonic oxygen.

Glucosides are favoured and the preferred compounds are diosgenyl β-D-glucoside, also known by its trivial name trillin, and hecogenyl β-D-glucoside or their mono-carboxylic acid derived esters. Notwithstanding the poor water solubility of these compounds (i.e. 5 mg of diosgenyl glucoside dissolves in 1 liter of water at room temperature to produce a colloidal solution and hecogenyl glucoside seems to be even less water soluble) it was surprising to find that they were medicinally effective (without showing the usual in vitro haemolytic effects usually found with saponins including the spiroketal steroid saponins) (6).

DETAILED INSTRUCTIONAL DESCRIPTION

The compounds of this invention can be synthesized by means of the known Koenigs-Knorr synthesis (7; W. Koenigs and E. Knorr: Chem. Ber., 1901, 34, 957-98%) or its modifications (8; C. Meystre and K. Mioscher: Helv. Chim. Acta, 1944, 27, 231-236. 9; R. B. Courow and S. Berstein: Org. Chem., 1971, 36, 863-870. 10; J. J. Schneider: Carbohyd. Res., 1970, 12, 369-389). 11; G. Wulff and G. Roehle: Angew. Chemie, 1974, 86, 173-87. 12; N. Weber: Chem. Phys. Lipids, 1977, 18, 145-148) or by the orthoester method (13; N. I. Uvarova: Carbohyd. Res., 1973, 27, 79-87) by treating 3β-hydroxyspiroketalsteroid aglycones with either a C-1 brominated- or a 1,2-orthoester mono- or disaccharide acetate in the presence of silver oxide or silver carbonate or other suitable catalysts. In addition the mono- or disaccharide glycoside of the invention may be obtained by controlled fermentation or acid hydrolysis procedures of the sugar richer spiroketalsteroid saponins.

The compounds of the invention can be incorporated by known procedures into food as well as into pharmaceutical products such as powders, pills, tablets, capsules, dragees, emulsions and solutions for injection, infusion or oral administration purposes. However, since the compounds are relatively insoluble (approximately 5 mg/1 l water at 25° C. for the glucosides of diosgenin and hecogenin) it is advantageous to incorporate them into pharmaceutical preparations in an amorphous, highly dispersed form; this is achieved by using known techniques such as heating, micronising, precipitation onto small-sized carrier particles etc. (The solid pharmaceutical products of this invention may be used in particle sizes of approximately 0.1 mm and preferentially of 0,06 mm and smaller dimensions).

In general the spiroketalins of this invention and especially diosgenyl β-D-glucoside and hecogenyl β-D-glucoside may be used in daily doses of 0,01–100 mg or even more.

Investigations indicate that the spiroketalins of the invention are useful in the treatment of inflammations due to various causes. Here as well it is important to realise that the presently available anti-inflammatory compounds such as corticosteroids, phenylbutazone, acetylsalicylic acid, indomethacin and others usually have to be administered in high doses (100 mg and more daily) which frequently induce definite adverse effects of varying degrees of severity, while the spiroketalins of the invention, whether given orally or parenterally, have not been observed to induce such adverse effects nor do they have to be taken in such high doses (usualy less than 1 mg daily). However, this advantage has to be viewed against the fact that their anti-inflammatory response is not pronounced or obvious within a short span of time.

The oral effectiveness of an anti-inflammatory agent is readily shown by administering it to animals (e.g. rats) either orally or parenterally before one of their hind paws is injected with a solution or suspension of an inflammation inducing substance such as kaolin, egg white, formaldehyde, carageenin or yeast. The anti-inflammatory effect of the spiroketalins was demonstrated by using a suspension of yeast, one of the milder inflammatory agents. Distinct reductions in the acute oedema formation of between 10–40% were observed depending on the dose and route of administration. In order to achieve such reduction with the glucosides of diosgenin, hecogenin and tigogenin doses of 500–1000 mg/kg body mass orally or 50–100 mg/kg intraperitoneally had been administered, 24 hours before the animals were challenged with fresh 2% yeast suspension in physiological saline.

The compounds of the invention are useful in the treatment of symptoms due to benign prostata hypertrophy.

The minimum effective daily spiroketalin dose for a human is approximately 0,03 mg, but up to 100 mg may be taken. It is recommended to use the compounds of this invention in daily doses of 0,3–0,75 mg in three or four single doses or in a single slow-release dose; the preferred daily dose is 0,30–0,45 mg in three single doses of 0,10–0,15 mg each. It has also been observed that a daily dose of less than 0,01 mg of these spiroketalins has no noticeable effect in the treatment of the various ailments and diseases. When animals are treated the required daily dose can be calculated by taking 75 kg as the average human weight.

It must also be remembered that spiroketalin esters are less effective than the spiroketalins themselves and slightly higher single- or daily doses of the esters must therefore be administered.

The following examples illustrate the invention:

EXAMPLE 1

The synthesis of diosgenyl β-D-glucoside (trillin) and other spiroketalins has been described (by 15; E. A. Sofowora and R. Hardman: Lloydia, 1976, 32, 141–143. 16; G. Wulff et al: Chem. Ber., 1972, 105, 1097–1110. 10; J. J. Schneider: Carbohyd. Res., 1970, 12, 369–389).

A well stirred mixture of silver carbonate (55,2 g) and a solution of diosgenin (41,4 g; mol. mass 414) in toluene (600 ml) was distilled until the collecting distillate was free of water. A solution of bromoacetylglucose (82,2 g) in toluene (100 ml) was then added dropwise to the stirred mixture, boiling continuing all the time with distillation in order to remove the water formed during the glucosidation reaction. At this state the reaction vessel is protected from light and the volume of the reaction mixture is kept constant at about 500 ml by adding extra dry toluene whenever necessary. After acetobromoglucose addition has been completed distillation is continued until no further water separates from the condensate. The reaction mixture is then filtered hot and the residue is washed with fresh, hot toluene. The combined filtrate and wash solutions are evaporated to dryness under vacuum and the residue is crystallised from ethanol or hexane. The yield of diosgenyl 3-β-D-glucoside tetraacetate (mol. mass 744) was 25,5 g or 34,3% 34,3% with m.p. 201°–203° C. and $(α)_D -76°$ (c 1,19, CHCl$_3$).

To a stirred solution of diosgenyl tetraacetate (10 g) in ethanol (600 ml) at 45° C. is rapidly added an ethanolic solution (15 ml) of sodium ethoxide (1 g Na in 100 ml abs. ethanol). The stirred mixture is allowed to react for 1 hour before water (2 l) is added and this mixture is then stirred for a further hour. The precipitated diosgenyl glucoside (mol. mass 576) is then filtered off and washed to neutrality with water before it is dried under vacuum at 100° C. for 12 hours. The yield amounted to 7 g or 90%; m.p. 277°–285° C. (crystallises at approx. 250° C.)

Similarly the following glycosides of hecogenin, tigogenin and diosgenin are examples of compounds falling within the scope of the present invention:

TABLE

|  | m.p. | $(α)_D$ | c | solvent |
|---|---|---|---|---|
| hecogenyl β-D-glucoside tetraacetate | 250–251° | −10° | 0,92 | CHCl$_3$ |
| tigogenyl β-D-glucoside tetraacetate | 204–205° | −50° | 1,00 | CHCl$_3$ |
| diosgenyl β-D-galactoside tetraacetate |  |  |  |  |
| diosgenyl β-D-maltoside octaacetate |  |  |  |  |
| diosgenyl β-D-lactoside octaacetate |  |  |  |  |
| tigogenyl β-D-galactoside tetraacetate | 270° | −44 | 1,0 | CHCl$_3$ |
| hecogenyl β-D-glucoside | 283–286° cryst. at approx. 260° | −22° | 1,43 | C$_5$H$_5$N |
| ticogenyl β-D-glucoside | 267–270° |  |  |  |
| diosgenyl β-D-galactoside | 224° dec. |  |  |  |
| diosgenyl β-D-maltoside |  |  |  |  |
| diosgenyl β-D-lactoside |  |  |  |  |
| tigogenyl β-D-galactoside | 236–238 | −65° | 0.9 | CHCl$_3$ |

EXAMPLE 2

The preparation of pharmaceutical products:

(a) The preparation of lactose-corn starch powders incorporating diosgenyl β-D-glucoside:

A boiling hot solution of diosgenyl glucoside (15 g) in chloroform (2,25 l) and ethanol (750 ml) is mixed with lactose powder (1 kg) of a particle size not exceeding 0,15 mm. The resulting slurry is dried with constant stirring and the impregnated lactose is reduced to its original particle size before it is mixed with corn starch (9 kg) and magnesium stearate (50 g). Capsules are readily filled with this mixture. Thus a capsule containing 100 mg of the mixture will carry approximately 0,15 mg diosgenyl β-D-glucoside, 10 mg of lactose, 90 mg of corn starch as well as 0,5 mg of magnesium stearate.

(b) The preparation of lactose granulates containing diosgenyl β-D-glucoside:

A boiling hot solution of diosgenyl glucoside (5 g) in ethanol (5 l) is mixed with lactose (3,32 kg) of a particle size not exceeding 0,15 mm. The agitated slurry is dried and the impregnated lactose is then reduced to the original particle size before it is converted into granules of 0,7-1-2 mm particle sizes. This granulated product is also suitable for filling into capsules, where for example a capsule containing 100 mg granulate carries 0,15 mg diosgenyl β-D-glucoside.

(c) The preparation of tablets containing diosgenyl β-D-glucoside:

A slurry, prepared by mixing lactose (900 g) with a hot solution of diosgenyl glucoside (1,25 g) in chloroform (1 l), is dried at room temperature and under a vacuum with constant agitation. The powdered product is then thoroughly mixed with potato starch (2,1 kg). The impregnated lactose-starch mixture is granulated by treating it with an aqueous solution (2,5 l) containing gelatine (250 g) and glycerine (5 g). The granulate, dried under reduced pressure at room temperature is converted by known methods into 400 mg tablets. Each tablet then contains 0,15 mg diosgenyl β-D-glucoside, 110,56 mg lactose, 257,97 mg potato starch, 30,31 mg gelatine and 0,61 mg glycerine.

(d) The preparation of hecogenyl β-D-glucoside containing dragees:

A slurry prepared by mixing lactose (1850 g), sucrose (300 g) and a hot solution of hecogenyl glucoside (450 mg) in chloroform (2 l) is dried under a vacuum at 30° C. The powdered product is granulated by known methods by adding an aqueous solution (1,6 l) of gelatine (40 g). The granulate, dried under reduced pressure at 45° C. and thoroughly mixed with magnesium stearate (10 g), is converted into 3000 pressed kernels which are finally coated to produce dragees. Every dragee then contains 0,15 mg hecogenyl β-D-glucoside, 616,67 mg lactose, 100,00 mg sucrose, 13,33 mg gelatine and 3,33 mg magnesium stearate.

Products as described under a-d above can also be prepared by using the following:
i. glycosides of the described spiroketalsteroids, but especially the β-D-glucosides of diosgenin hecogenin and tigogenin;
ii. glucose, ascorbic acid, talc or silica oxide as carriers for the spiroketalins or any other pharmaceutically acceptable carriers;
iii. the contents of the active spiroketalins in each unit dose can be adjusted to any value between 0,01 mg and more;
iv. the auxilliary substances described in a-d can be altered according to accepted pharmaceutical practices;
v. at each stage of the production processes described in a-d can other pharmaceutically active substances be added or incorporated into the final product.

(e) Preparation of an ointment containing hecogenyl β-D-glucoside:

To a mixture of hecogenyl glucoside (1 g) worked into emulsifying cetyl alcohol (90 g) is added viscous paraffin (105 g) and white vaseline (105 g) before melting the complete mixture on a 60° C. waterbatch. Into this melt is stirred water (699 g) in small portions at a time. The final mixture is stirred until cold to provide an ointment containing 0,1% spiroketalin.

(f) Preparation of a cream containing tigogenyl β-D-glucoside:

Woolwax alcohol (500 g) into which tigogenyl glucoside (1 g) has been incorporated is heated to about 50° C. on a water bath. To the resulting melt water (499 g) is added in small portions with constant stirring. The final cream is stirred until it reaches room temperature; during this process sufficient water is added to replace evaporation losses. This cream contains 0,1% spiroketalin. Similarly other spiroketalins, but especially the of diosgenin, hecogenin and tigogenin, may be incorporated into creams, ointments and lotions which may also incorporate other pharmaceutically active, alternative and acceptable substances.

EXAMPLE 3

Preparation of pharmaceutically acceptable solutions.

A solution containing diosgenyl β-D-glucoside:

A polyvinylpyrrolidone (PVP) solution in distilled water (4 liter) and at 65° C. was stirred into a boiling solution of diosgenyl glucoside (600 mg in 6 liter ethanol). The cooled (±22° C.) 60% aqueous ethanol solution was filled into 250 ml medicine bottles, provided with instructions to patients that doses of a half teaspoonful had to be taken daily (i.e. 3×2,5 ml daily). This provided 40×250 ml bottles each containing approximately 100×2,5 ml doses which was sufficient for a 33 day period.

Every half teaspoon contains 0,15 mg spiroketalin, 2,5 mg PVP and 1,5 ethanol in its 2,5 ml overall volume.

In general, to avoid the problem of unstable solutions it is advisable not to exceed concentrations of 7,5 mg spiroketalin and 100 mg PVP per 100 ml of solution, i.e. not more than 0,1875 mg of spiroketalin can be provided by a 2,5 ml dose.

According to the above method other spiroketalins may be brought into solution. However, because of the small solubility of these compounds exposure to low temperature should be avoided in order to prevent possible precipitation or floculation.

EXAMPLE 4

(a) ANIMAL TOXICITY

Individually housed groups of ten male Sprague-Dawley rats were treated orally with single doses of hecogenin 3-β-D-glucoside or diosgenin 3β-D-glucoside. The poorly water soluble test substances were made up in an aqueous Tylose$^R$ dispersion for homogeneity.

A suitable concentration which allowed the administration of the relevant dose at the rate of 1,0 ml/100 g body weight was prepared immediately before use. Doses ranging from 125 mg/kg to 1250 mg/kg of the agents were tested. The observation period was 14 days after which the animals were sacrificed and a macroscopic examination of some tissues was carried out. Food and water was offered ad libitum.

RESULTS

No animal from any group died during the predetermined observation period. A slight decrease of body weight during the first 72 hours was observed in the groups which received the largest dose (i.e. 1250 mg/kg). At termination all groups exhibited similar body weights. The food-intake was slightly lower in the highest dosage groups during the first 2 days, however, no decrease in fluid intake was noted. On the contrary there was a slight (not significant) increase in the daily water consumption.

No macroscopic visible changes were observed in any of the groups. Special attention was paid to possible lesions in the gastro-intestinal tract, but no indication of any active or healing ulcers were detected at the time of necropsy.

In conclusion, it may be stated that both test compounds, i.e. hecogenin 3$\beta$-D-glucoside and diosgenin 3-$\beta$-D-glucoside were well tolerated by Sprague-Dawley rats at single oral doses of 125,0; 312,5; 625,0 and 1250 mg/kg.

(b) Standard laboratory chow was thoroughly mixed with 0,1% diosgenyl glucoside or hecogenyl glucoside and the mixtures were fed to groups of 20 young male Sprague-Dawley rats weighing approximately 150 g. No mortality occurred during a 100 day observation period. The growth curves in the treated groups were similar to that observed in the control group. Ten rats from each group were autopsied and the organs and some body tissues examined by macroscopic and microscopic techniques. No drug-related pathological changes were detected in any tissues.

EXAMPLE 5

According to our present day knowledge prostanoids (the various prostaglandins, and some closely related compounds and precursors such as arachidonic acid, endoperoxides, thromboxanes, prostacyclines etc.) play most probably an important role in the initiation of rheumatoid arthritis and other inflammatory diseases. The compounds of this invention were, therefore, examined for their possible prostenoid-regulating properties with the use of a pharmacological method.

A comparison of erysipelas-induced arthritis in the rat with rheumatoid arthritis in humans shows that there is considerable correspondence of most of the individual morphological changes. The investigation was carried out according to Schulze et al (17 in Betr. Path., 1975, 154, 1–26 and 27–51). Erysipelas arthritis is reproducible in nearly 100% of the rats given a single subcutaneous injection of E. insidiosa. Erysipelas arthritis always afflicts several joints with the same intensity in both major and minor limb joints, besides the coagulopathy and the pathological changes produced in the cardio-vascular system. Proliferating processes occur after 3 months in all surviving animals subjected to experimental erysipelas arthritis.

In order to test the spiroketalins of this invention the following parameters of the erysepilas arthritis model were used to evaluate their activities:

1. Paw volumes:

Arthritis in the rat is exhibited by a periarticular oedema which appears in animals weighing 150 g as from the 3rd day, while the phenomena can be observed as from the 5th day in animals weighing approximately 200.

2. Kidney (protein elimation):

Nephroses induced through microthrombi can appear in approximately 3–40% of the animals on the 7th–8th day.

3. Eye:

Inflammation opaquacy appears in the cornea around the 8th day.

4. External sex organs and tailtip:

Thrombi induced necrosis starting on the 6th–8th day.

5. Aorta:

Fibrin-rich thrombi develop on aorta intima between the 6th and 11th day. The largest spread extended area can be observed around the 8th day.

Male Wistar rats between 155–185 g were used for these trials. The animals, kept in single cages, received a standard rat diet (Ssniff R) and water ad libitum. Room temperature was kept at 22° C., and the relative humidity varied between 50–60%. Daily illumination lasted for 12 hours. The animals had been acclimatized for 10 days prior to the commencement of the investigation.

An erysopelothrix insidiosa serotype B-strain T28 was used to challenge the animals and a single 2 ml dose (ca 100–200 million germs) was administered subcutaneously. The examined spiroketalins were suspended in sterile physiological saline and administered at the rate of 3×10 mg/kg per day. Treatment continued from the day of challenge, either to the end of the trial or the death of an animal, at the rate of 5×per week.

RESULTS

Some interesting and unexpected informations are obtained from the study with erysipelas induced arthritis. The most relevant data are exhibited in the following TABLES:

| COMPOUND | AORTIC THROMBI Degree of severity | Present in % of rats |
|---|---|---|
| CONTROL | 2,60 (± 1,35) | 90 |
| Hecogenyl Glucoside | 1,38 (± 1,51) | 50 |
| Diosgenyl Glucoside | 1,33 (± 1,66) | 44 |
| Sitosteryl-$\beta$-D-Glucoside | 2,00 (± 1,63) | 70 |

| | CORNEAL LESIONS | | | | | | |
|---|---|---|---|---|---|---|---|
| COM- | Degree of se- | Present in % of rats days | | | | | |
| POUND | verity | 1 | 6 | 8 | 12 | 15 | 19 | 20 |
| CONTROL | 2,34 | 0 | 100 | 100 | 100 | 100 | 100 | 100 |
| Hecogenyl Glucoside | 0,89 | 0 | 87,5 | 100 | 100 | 100 | 20 | 0 |
| Diosgenyl Glucoside | 1,05 | 0 | 85,7 | 100 | 100 | 50 | 25 | 0 |
| Tigogenyl Glucoside Sitosteryl-$\beta$-D-Glucoside | 1,20 | 20 | 90 | 100 | 100 | 17 | 25 | 0 |

The parameters for aorta thrombi have been evaluated according to the following key originally described by Schulz et al. Beitrag. Path., 154, 1–26 and 27–51, 1975.

KEY FOR CLINICAL AORTA THROMBI FINDINGS

0 = No change
1 = Very slight changes
2 = Slight to medium changes

3=Medium to severe changes
4=Severe changes

Distinct reduction in both the degree of severity and percentage of animals affected by aortic thrombi and corneal lesions (opaquacy) was observed and can clearly be noted from the TABLES.

EXAMPLE 6

Further Proof of activity as PGS Inhibitor

The activity of the compounds as PGS inhibitor was proved according to the method described by A. L. Willis. Conditions of trial are described for example in Proceedings of a Workshop held during the VIIIth European Dermatology Congress Helsinki 1975.

Siliconized cuvettes of the aggregometer are used at a temperature of 37° C. as incubation vessels in which an arachidonate solution was rapidly stirred with a PG synthetase enzyme system, usually from sheep vesicular gland. To this solution in the cuvette there is added anticoagulated platelet rich plasma, previously warmed to 37° C. Light transmission through the cuvette was recorded immediately after addition. The comparison sample showed a significant peak in the platelet aggregation after 45 seconds of incubation time which proved the formation of $PGE_2$ and $PGF_{2a}$ and the corresponding platelet aggregation.

In the test samples containing 0.00001% spiroketal-steroid glycoside no platelet aggregation occurred. This clearly shows that the formation of PGs via endoperoxide compounds from arachidonate was inhibited.

REFERENCES

1. M. H. Briggs and J. Brotherton: Steroid saponins, spirotanol, Steroid Biochemistry and Pharmacology, Academic Press, 1970 pp 288–294.
2. R. Tschesche and G. Wulff: Chemie und Biologie der Saponine, Forts. Chem. Org. Naturp., 1973, 30, 461–606.
3. J. L. Diaz-Zagoya, J. Laguna and J. Guzman-Garcia: Studies on the regulation of cholesterol metabolism by the use of the structural analogue diosgenin; Biochem. Pharmacol; 1971, 20, 3473–3480.
4. J. Laguna, A. Gomez-Puyou, A. Pema and J. Guzman-Garcia: Effect of diosgenin on cholesterol metabolism; J. Atheros. Res., 1962, 2, 459–470.
5. DT-OS No. 2348176, U.S. Pat. No. 3,890,438
6. T. R. Govindachari: Chemical and biological investigations on the extracts and constituents of some Indian plants; 1st Internatl. Congr. Res. Med. Plants, Muenich, 6–10th Oct. 1976
7. W. Koenigs and E. Knorr: Ueber einige Derivate des Traubenzuckers und der Galactose; Chem. Ber., 1901, 34, 957-et.seq
8. C. Meystre and K. Miescher: Zur Darstellung von Saccharidderivaten der Steroide; Helo. Chim. Acta, 1944, 27, 231–236.
9. R. B. Conrow and S. Bernstein: An improved Koenigs-Knorr synthesis of aryl glucuronides using cadmin carbonate, a new and effective catalyst; Org. Chem., 1971, 36, 863–870.
10. J. J. Schneider: Preparation and properties of some new steroid B-D-glucopyranosides, P-D-glucopyranosiduronic acids, and derivatives; Carbohyd. Res. 1970, 12, 369–389.
11. G. Wulff and G. Röhle: Ergebnisse und Probleme der O-Glykosidsynthese; Angew.Chem. 1974, 86, 173–187.
12. N. Weber: Eine einfache Synthese acetylierter Steryl B-Glykoside; Chem. Phys. Lipids, 1977, 18, 145–148.
13. N. I. Uvarova, G. L. Oshitok and G. B. Elyakov: Synthesis of steroid and triterpenoid glycosides by the orthoester method; Carbohyd. Res. 1973, 27, 79–87.
14. K. H. Pegel Therapeutisches kompositum; DT-OS No. 21133215; K. H. Pegel Therapeutic agent; GB No. 1298047.
15. E. A. Sofowora and R. Hardman: Synethesis of 3B-glucosides of diosgenin, yamogenin and gitogenin; Lloydia, 1976, 32, 141–143.
16. G. Wulff, G. Roehle and U. Schmidt: Neuartige Silbersalze in der Glykosidsynthese; Chem. Ber., 1972, 105, 1097–111o.

I claim:

1. An anti-inflammatory composition characterized in that it is in the form of a tablet or capsule and includes a pharmaceutically acceptable carrier and a compound of the formula where:
1. either a double bond starts at C-5 or C-5 carries an alpha hydrogen (5d),
2. Z is a saccharide selected from the group consisting of glucose, maltose, galactose and lactose which may be partially or completely esterified with a pharmaceutically acceptable monocarboxylic acid,
3. R represents either two hydrogens or a ketonic oxygen, in an amount sufficient to cause an anti-inflammatory action.

2. A composition according to claim 1 characterised in that the compound is chosen from the group consisting of diosgenyl-β-D-glycoside and hecogenyl-β-D-glycoside, and their pharmaceutically-acceptable esters.

3. A composition according to claim 1 in dosage form characterised in that the compound is present in unit dosage form to the extent of between 0.3 and 0.75 mgm.

4. An anti-inflammatory composition in the form of a tablet or capsule and including a compound selected from the group consisting of hecogenin and tigogenin glucosides, maltosides and lactosides, and esters thereof in an amount sufficient to cause an antiinflammatory action.

5. A composition according to claim 1 wherein the saccharide moiety is selected from the group consisting of β-D-glucoside, β-D-glucoside acetate, β-D-galactoside acetate, β-D-maltoside acetate, β-D-lactoside acetate, β-D-galactoside, β-D-maltoside and β-D-lactoside.

6. A composition according to claim 5 wherein the compound is selected from the group consisting of hecogenyl, tigogenyl and diosgenyl glucosides, maltosides and lactosides.

7. A composition according to claim 1 wherein when the saccharide moiety is esterified it is an acetate.

8. A method of treating a disease caused by an inflammatory condition characterized by the administration to the patient a composition including a pharmaceutically acceptable carrier and an anti-inflammatory effective amount of a compound of the formula

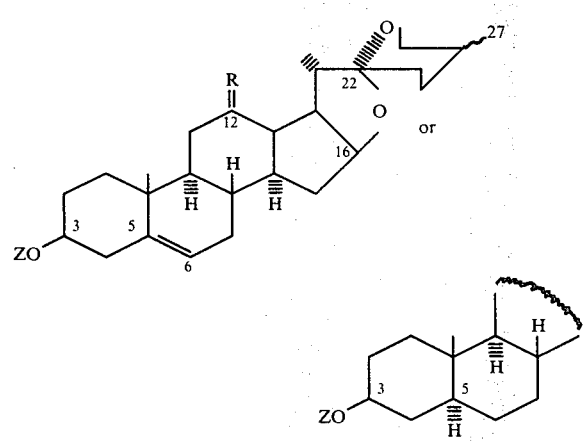

where:
1. either a double bond starts at C-5 or C-5 carries an alpha hydrogen (5d),
2. Z is a saccharide selected from the group consisting of glucose, maltose, galactose and lactose which may be partially or completely esterified with a pharmaceutically acceptable monocarboxylic acid,
3. R represents either two hydrogens or a ketonic oxygen.

9. A method of treating a disease caused by inflammatory condition characterized by the administration to the patient of an anti-inflammatory-effective amount of a composition including a pharmaceutically acceptable carrier and a compound chosen from the group consisting of diosgenyl-β-D-glycoside and hecogenyl-β-D-glycoside and their pharmaceutically acceptable esters.

10. A method of treating benign prostate hypertrophy comprising administering to a patient a composition including a pharmaceutically acceptable carrier and an amount of a compound of the formula

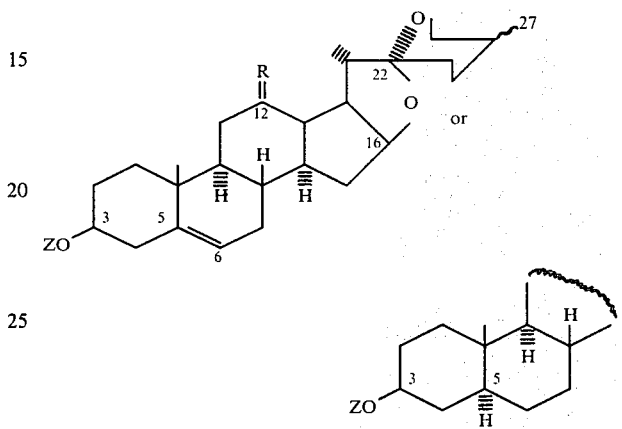

where:
1. either a double bond starts at C-5 or C-5 carries an alpha hydrogen (5d),
2. Z is a saccharide selected from the group consisting of glucose, maltose, galactose and lactose which may be partially or completely esterified with a pharmaceutically acceptable monocarboxylic acid,
3. R represents either two hydrogens or a ketonic acid effective to treat benign prostate hypertrophy.

11. A method according to claim 8 wherein when the saccharide moiety is esterified it is an acetate.

* * * * *